US007790462B2

(12) United States Patent
Fournier et al.

(10) Patent No.: US 7,790,462 B2
(45) Date of Patent: Sep. 7, 2010

(54) REACTION VESSEL SUPPORT HAVING PIVOTING PLATES, AN ANALYZING DEVICE COMPRISING A SUPPORT OF THIS TYPE, AND CORRESPONDING ANALYSIS METHOD

(75) Inventors: Laurent Fournier, Versailles (FR); Bruno De Bastiani, Paris (FR)

(73) Assignee: Bio-Rad Pasteur, Marnes la Coquette (FR)

( * ) Notice: Subject to any disclaimer, the term of this patent is extended or adjusted under 35 U.S.C. 154(b) by 382 days.

(21) Appl. No.: 11/918,738

(22) PCT Filed: Apr. 11, 2006

(86) PCT No.: PCT/FR2006/000799

§ 371 (c)(1),
(2), (4) Date: Oct. 18, 2007

(87) PCT Pub. No.: WO2006/111634

PCT Pub. Date: Oct. 26, 2006

(65) Prior Publication Data

US 2009/0075385 A1   Mar. 19, 2009

(30) Foreign Application Priority Data

Apr. 20, 2005   (FR) .................................. 05 03968

(51) Int. Cl.
*G01N 35/02* (2006.01)
*B65G 1/00* (2006.01)
*F16M 11/00* (2006.01)
(52) U.S. Cl. ............... 436/47; 414/331.01; 414/331.14; 414/331.18; 248/678; 211/129.01; 422/63
(58) Field of Classification Search ................... 436/47; 248/678
See application file for complete search history.

(56) References Cited

U.S. PATENT DOCUMENTS

| 5,306,510 A | * | 4/1994 | Meltzer | ....................... 422/65 |
| 6,919,044 B1 | * | 7/2005 | Shibata et al. | ................ 422/63 |
| 2003/0059287 A1 | * | 3/2003 | Warhurst et al. | ....... 414/331.14 |
| 2004/0094575 A1 | * | 5/2004 | Toi et al. | ..................... 222/135 |
| 2004/0166022 A1 | | 8/2004 | Barzilai et al. | |

FOREIGN PATENT DOCUMENTS

EP         0 317 677 A    5/1989
WO    WO 2004/003219 A2   1/2004

* cited by examiner

*Primary Examiner*—Jill Warden
*Assistant Examiner*—Jennifer Wecker
(74) *Attorney, Agent, or Firm*—Jacobson Holman PLLC

(57) ABSTRACT

This reaction vessel support is of the type comprising at least one supporting plate (46, 48) designed to take one or more reaction vessels, and mounted rotatably about an axis of rotation (R).

In one aspect of the invention, the support comprises at least one control member (94, 96) comprising releasable means (100) of coupling to a movable actuating element (40) of an actuator (10), in such a way as to enable the control member (94, 96) to be moved by the actuator (10), with the control member (94, 96) and the supporting plate (46, 48) being connected together in such a way that a movement of the control member (94, 96) by the actuator (10) is able to bring about a rotation of the supporting plate (46, 84) about the axis of rotation (R) in at least one direction of rotation.

Of particular application to supports for microassay plates comprising wells laid out in a matrix arrangement.

15 Claims, 9 Drawing Sheets

REACTION VESSEL SUPPORT HAVING PIVOTING PLATES, AN ANALYZING DEVICE COMPRISING A SUPPORT OF THIS TYPE, AND CORRESPONDING ANALYSIS METHOD

This is a 371 of PCT/FR2006/000799, filed Apr. 11, 2006.

The present invention relates to a reaction vessel support of the type comprising a chassis designed to be mounted in an analyzing device and a supporting plate designed to take the vessel, the supporting plate being mounted rotatably on the chassis about an axis.

Many chemical, biological and biochemical analyses require that chemical, biological or biochemical compounds or reagents in liquid form be brought into contact with one or more samples and incubated. For example, many biological assays involve reacting samples of serum, plasma or blood with liquid preparations of enzymes (enzyme assays or tests), or of antibodies or antigens (immunological assays or tests), or of nucleic acids (hybridization assays or tests with or without nucleic amplification), etc.

These assays or tests are normally done in reaction vessels in which the samples and reagents are mixed together. An example of such a container is a microassay tray comprising a plurality of wells arranged in a matrix layout consisting of rows and columns.

The wells are advantageously filled automatically by an analyzing device comprising a reagent dispensing unit having pipettes designed to deposit samples and/or reagents in the wells.

Document US 2004/0094575 discloses an analyzing device comprising a row of pipettes carried by a rotary mechanism capable of pivoting the pipettes through a one-quarter revolution about a vertical axis, in such a way as to selectively align the pipettes with the rows or columns of a microassay tray.

Such a unit can perform matrix-style dispensing of reagents into the wells i.e. two-dimensional distribution, by for example filling the wells row by row with a first reagent, and column by column with a second reagent. Matrix dispensing is useful in many tests and assays, for example tests and assays targeting medicinal molecules.

However, that device is complicated and expensive.

It is an object of the invention to provide a simple unit that is inexpensive to manufacture and can fill a reaction vessel quickly.

For this purpose, the invention provides a support of the aforementioned type, characterized in that it comprises at least one control member comprising releasable means of coupling to a movable actuating element of an actuator of the analyzing device, in such a way as to enable the control member to be moved by the actuator, with the control member and the supporting plate being connected together by mechanical drive elements, in such a way that a movement of the control member by the actuator is able to bring about a rotation of the supporting plate about the axis of rotation in at least one direction of rotation.

In another embodiment, the support comprises one or more of the following features, taken in isolation or in any technically possible combination:
  the mechanical drive elements are housed inside the chassis;
  the supporting plate is movable between two extreme positions forming an angle of 90° to each other;
  it comprises return elements designed to return the supporting plate to a first extreme position when the supporting plate is between the first extreme position and a particular intermediate position between the two extreme positions, and to return the supporting plate to the second extreme position when the supporting plate is between the second extreme position and the intermediate position;
  the return elements comprise a component linked in movement to the supporting plate, and an elastic return member extending between the component and a fixed attachment on the chassis, the component possessing a trajectory which passes through a position of greatest distance from the attachment when the supporting plate is in the intermediate position;
  the control member or each control member is slidably mounted on the chassis, and in that the drive elements comprise a roller and a lever, one being connected to the control member or to each control member, and the other being connected to the supporting plate;
  it comprises a control member for moving the supporting plate in one direction of rotation, and another control member for moving the supporting plate in the opposite direction of rotation, the releasable means of coupling the control members being designed to be selectively engaged by the movable actuating element of an actuator belonging to the analyzing device;
  the supporting plate comprises means of identification enabling the orientation of the supporting plate about its axis of rotation to be identified.

The invention also relates to an analyzing device comprising a table and a dispensing unit, the latter comprising a dispensing head that is movable relative to the table and possessing a row of pipettes designed to draw up, retain and/or eject liquid, said device being characterized in that it comprises at least one reaction vessel support as defined above, the chassis being designed to be mounted on the table in such a way as to allow a reaction vessel carried by the support to be filled, and at least one actuator comprising a movable actuating element designed to be engaged with the releasable coupling means of the control member or each control member of the support.

In other embodiments, the device comprises one or more of the following features, taken in isolation or in any technically possible combination:
  the actuator and the support comprise releasable coupling means for moving the support relative to the table;
  the actuator comprises means for reading identification codes on a reaction vessel;
  the means of identification of the supporting plate are of the same type as the identification codes of the reaction vessels designed to be placed on the support.

The invention also relates to a method of analyzing samples distributed in wells in a vessel carried by the support, using an analyzing device as defined above, comprising the following steps:
  controlling the actuator to act on the control member or a control member of the support in order to place the supporting plate in a first position;
  using the dispensing unit to fill the wells;
  controlling the actuator to act on the control member or a control member of the support in order to place the supporting plate in a second position by pivoting it through an angle of approximately 90° about the axis of rotation of the plate relative to the chassis; and
  using the dispensing unit to fill at least some wells.

The invention also relates to a computer program product recordable on a digital data medium or in a computer, comprising software steps for executing the method as defined above, when the program is executed on a computer.

A clearer understanding of the invention and its advantages will be acquired from reading the following description, given purely by way of example, and referring to the accompanying drawings, in which.

Figure 1:
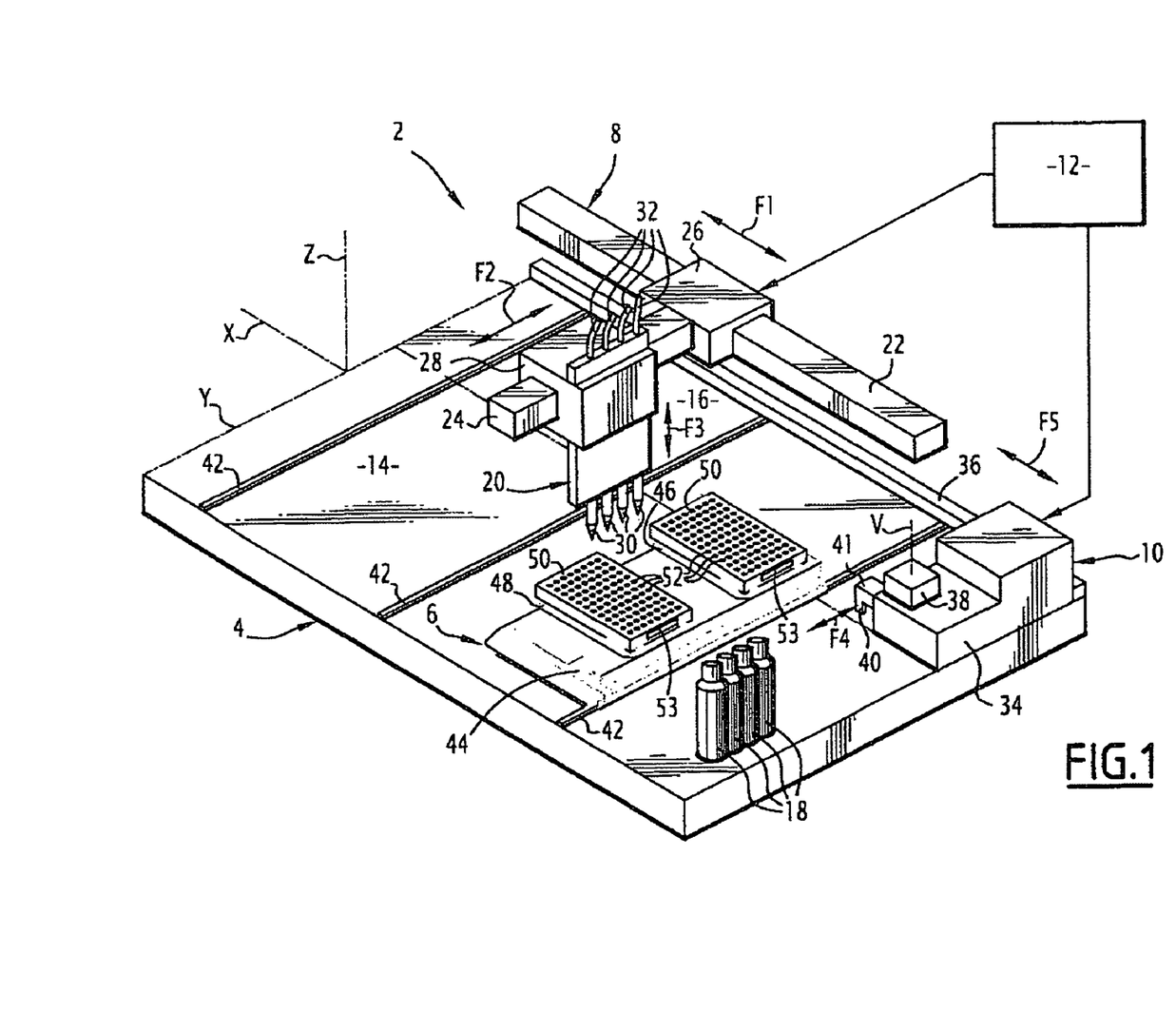
FIG. 1 is a schematic perspective view of an automatic analyzing device comprising a support according to the invention, with rotary support plates.

As shown in FIG. 1, the analyzing device 2 comprises an substantially horizontal table 4, a reaction vessel support 6 mounted removably on the table 4, a liquid dispensing unit 8 capable of automatically taking liquids from one point of the table 4 and dispensing them at another point of the table 4, an actuator 10, mounted movably on the table 4, for identifying analysis vessels placed on the support, and a control unit 12 for controlling the dispensing unit 8 and the actuator 10.

The table 4 is rectangular and elongated in a substantially horizontal direction X. The table 4 is separated into two adjacent areas extending along the X direction (and separated symbolically by a chain line): a storage area 14 containing the support 6, and a movement area 16 in which the actuator 10 moves.

Reagent vessels 18 are located in area 14.

The dispensing unit 8 comprises a dispensing head 20 mounted so as to be able to move translationally over area 14 in three directions: the X direction, a substantially vertical Z direction, and a direction Y perpendicular to the X and Z directions.

For this purpose the dispensing unit comprises a fixed horizontal bar 22 extending in the X direction above area 16, a horizontal arm 24 extending in the Y direction above area 14, with an end portion 26 mounted on the bar 22 and able to move translationally in the X direction along it (arrow F1), and a carriage 28 mounted on the arm 24 and able to move translationally along it in the Y direction (arrow F2). The head 20 is mounted on the carriage 22 and able to move translationally along it in the Z direction (arrow F3).

Mounted in the head 20 are several, for example four, pipettes 30 aligned in the Y direction.

As known per se, each pipette 30 is designed to selectively draw up liquid into the pipette 30, hold the liquid in the pipette 30, and expel the held liquid from the pipette 30. In order to give it independent control, each pipette 30 may for example be connected to a hydraulic control circuit (not shown) via a tube 32.

As known per se, the spacing in the Y direction between the pipettes 30 is adjustable so that liquid can be simultaneously drawn from or dispensed into several vessels with different spacings.

The actuator 10 comprises a base 34 mounted in area 16 and able to move translationally in the X direction (arrow F5) along a rail 36 fixed to one edge of the table 4; an optical reader 38 hinged to the base 34 about an axis V parallel to the Z direction; and a drive finger 40 mounted on a shuttle 41 connected to the base 34 and able to move translationally along it in the Y direction (arrow F4). The actuator 10 comprises drive means (not shown) so that it is possible to control the positions of the base 34 along the rail 36, the reader 38 about the V axis, and the shuttle 41 relative to the base 34 in the Y direction. The control unit 12 is connected to the dispensing unit 8 and to the actuator 10 for the purpose of controlling them.

The control unit 12 comprises a memory for storing instructions, which may be in the form of a computer program, and a microprocessor adapted to execute the computer program.

A number of guide tracks 42 are mounted on the areas 14, 16 of the table 4. The tracks 42 are parallel to each other, extend in the Y direction, and are spaced out at more or less regular intervals.

The support 6 comprises a chassis 44, and two plates 46, 48 each designed to take one reaction vessel.

A microassay tray 50 forming a reaction vessel is carried by each plate 46, 48.

Each tray 50 is rectangular and comprises ninety-six wells 52 designed to take samples and liquid reagents. They are laid out matrix-fashion in twelve columns.

Each tray 50 is given identifying bar codes 53 on two adjacent narrow edges (only one such edge being visible).

Figure 2:
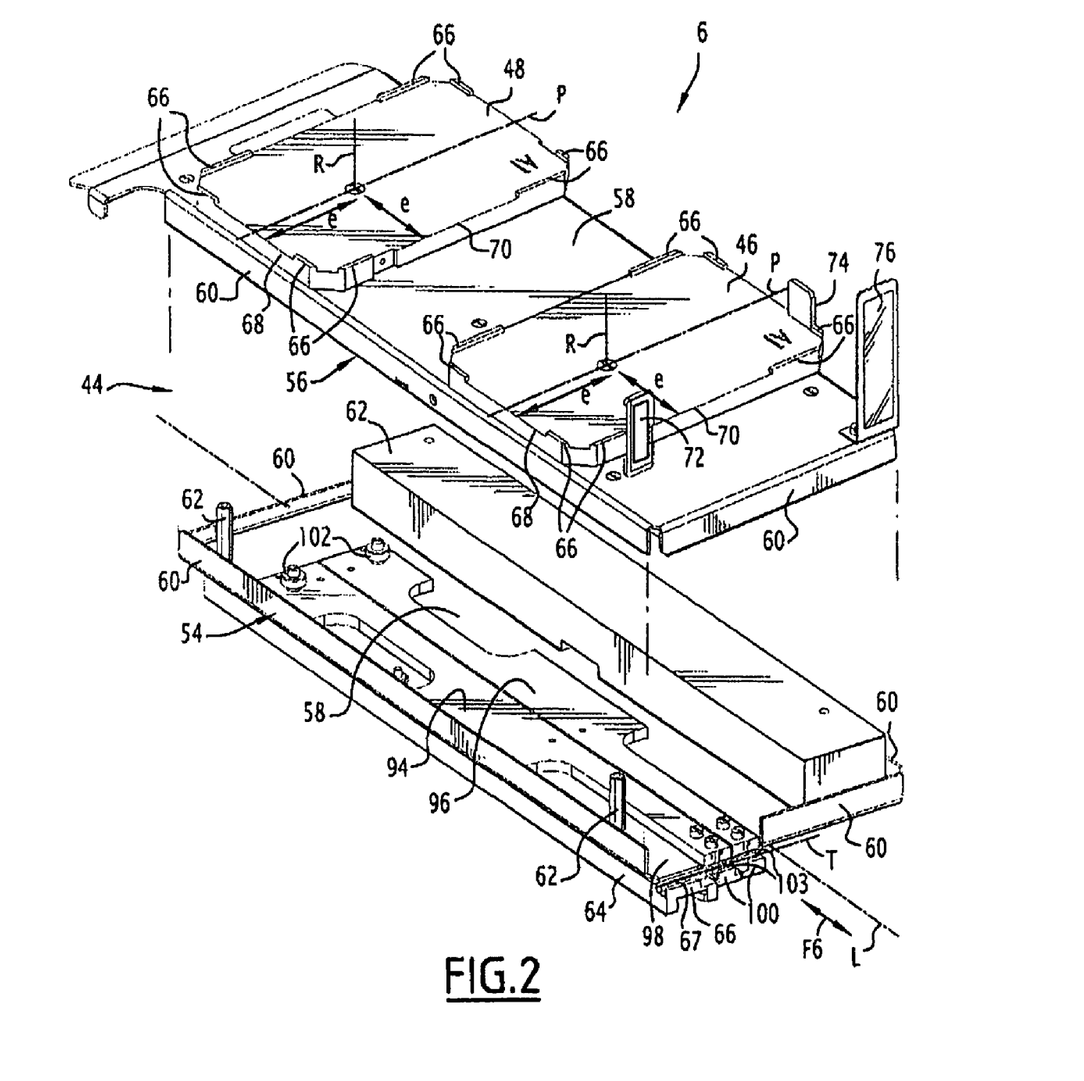
FIGS. 2 and 3 are exploded schematic perspective views of the support shown in FIG. 1, seen from different angles, illustrating a control system for controlling the rotation of the plates.
Figure 3:
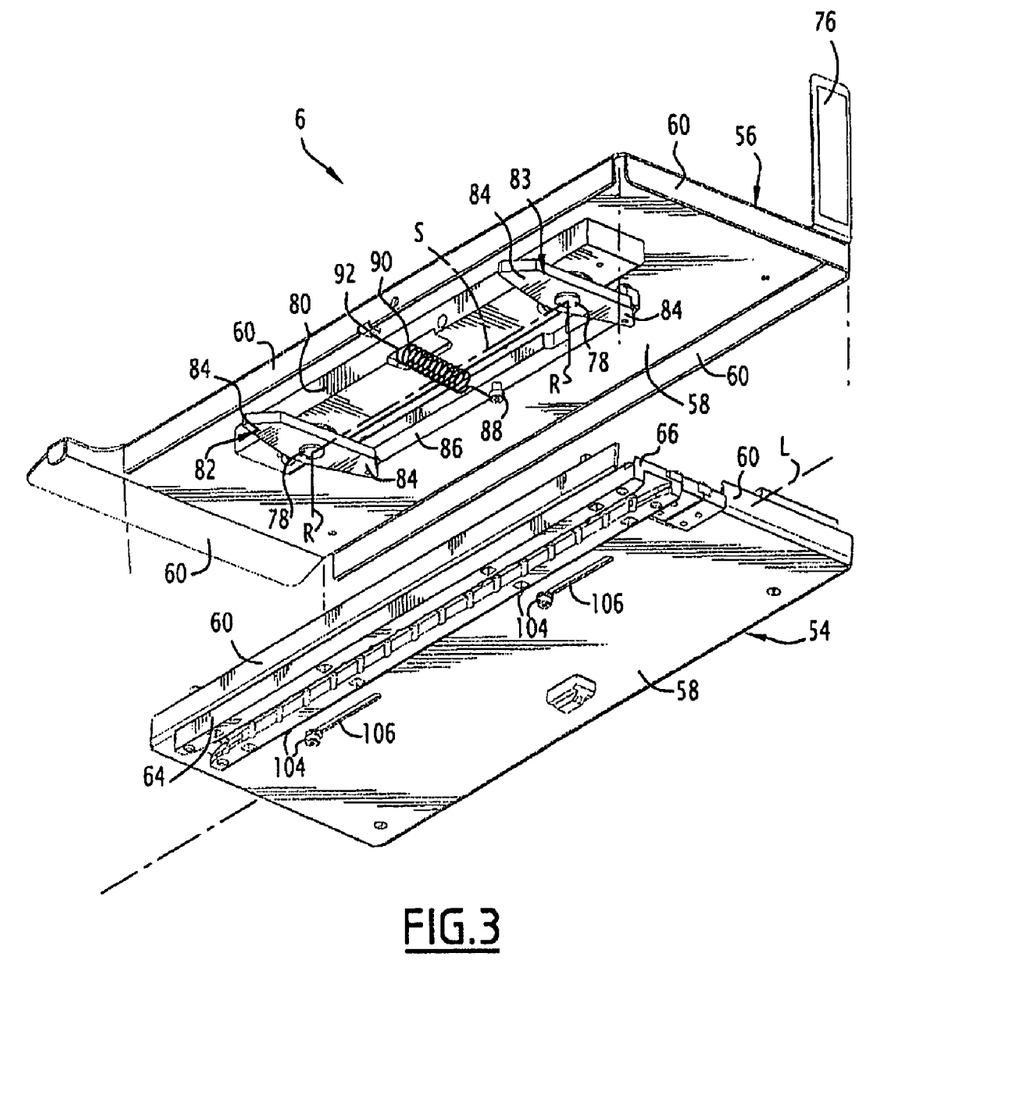

As shown in FIGS. 2 and 3, where only support 6 is shown, the chassis 44 is in the shape of a right-angled parallelepiped elongated in a longitudinal direction L.

The chassis 44 comprises a metal lower half 54 and a metal upper half 56 defining between themselves an internal space.

Each half 54, 56 comprises an essentially flat central portion 58 with peripheral flanges 60 bent toward the other half 54, 56. The flanges 60 define a narrow edge of the chassis 44 when the halves 54, 56 are brought together.

The halves 54, 56 are connected together by means of spacers 62.

A mounting rail 64 (FIG. 3) is attached to the underside of the lower half 54 along a longitudinal edge of the central portion 58. The rail 64 is designed to engage with a track 42 (FIG. 1).

At one end of the rail 64 is a hook 66 projecting beyond a transverse edge of the central portion 58. The hook 66 comprises a coupling slot 67.

The plates 46, 48 (FIG. 2) pivot on the upper half about mutually parallel axes R intended to be essentially vertical when the support 6 is mounted on the analyzing device 2.

Each plate 46, 48 is basically rectangular and is elongate in a direction P, with peripheral locating flanges 66 on an upper face away from the chassis 44. The corners of each plate 46, 48 are beveled.

For each plate 46, 48, the axis R is situated at an equal distance e from two adjacent edges 68, 70 of the plate 46, 48. These edges will be termed "reference edges".

The plate 46 comprises, on two adjacent edges, tabs 72, 74 bearing marks in the form of bar codes readable by the reader. One tab 72 is attached to the long reference edge 70, and the other tab 74 is attached to an edge opposite the short reference edge 68.

A visual mark "A1" indicating the first well of a microassay tray is etched on one corner of each plate 46, 48 to help an operator correctly position a microassay tray on the plate 46, 48.

When a microassay tray 50 (FIG. 1) is correctly positioned on the plate 46, 48, the identification codes 53 (FIG. 1) of the tray 50 (FIG. 1) are situated over the reference edges 68, 70 of the plate 46, 48.

The upper half 56 is given a tab 76 bearing an identification mark in the form of a bar code readable by the reader 38 (FIG. 1).

As can be seen more clearly in FIG. 3, each plate 46, 48 is mounted on one end of a shaft 78 passing through the upper half 56, and mounted rotatably on a reinforcing bar 80 attached to the underside of the upper half 56.

The support 6 comprises, located inside the chassis 44, a control system for causing the plates to rotate.

The control system comprises a lever 82, 83 mounted on each shaft 78, at the opposite end of the shaft 78 from the plate 46, 48 (FIG. 2), using a tightening screw.

The lever 82 extends substantially at right angles to the axis R of the corresponding shaft 78 and comprises two diametrically opposed arms 84.

The levers 82, 83 are approximately parallel to each other.

The levers 82, 83 are connected by a motion-transfer link 86 which pivots at each end on one arm 84 of one of the levers 82, 83 in such a way that the levers 82, 83 will rotate in a synchronized fashion. In operation, lever 83, hereinafter the "driven lever", imitates the movement of lever 82, hereinafter the "drive lever".

The link 86 is provided at about its mid-point with a fixing pin 88. An elastic return spring 90 is attached at one end to the pin 88 and at the other end to an attachment 92 on the opposite side of the line S passing through the axes R from the pin 98. The attachment 92 is formed integrally from a longitudinal flange 60 of the upper half 56.

As FIG. 2 shows more clearly, the control system comprises two control rods 94, 96 mounted on the lower half 54 inside the chassis 44.

Each rod 94, 96 possesses an elongate form in the L direction and comprises a hook 100 at one end projecting out of the chassis 44 through an opening 98 formed in a transverse flange 60 on the lower half 54 situated over the hook 66. The other end of each rod 94, 96 has a roller 102.

Each hook 100 possesses a coupling slot 103.

Each rod 94, 96 is mounted on, and slides in the L direction on, the lower half 54 (arrow F6). For this purpose, as shown in FIG. 3, each rod 94, 96 has runners 104 sliding in elongate through slots 106 in the lower shell 54, only slots 106 associated with rod 96 being visible in FIG. 3.

Each rod 94, 96 can move independently of the other rod between a rest position (FIGS. 2 and 3), in which the rod 94, 96 is mostly inside the chassis 44, and only its hook 100 is projecting from the opening 98, and an active position in which the rod 94, 96 is partially drawn out of the chassis 44 in the L direction. Each rod 94, 96 is returned to its rest position by a spring (not shown).

The rods 94, 96 are arranged so that the roller 102 of one rod 94 faces one arm 84 of the drive lever 82, in the L direction, and the roller 102 of the other rod 96 faces the other arm of the drive lever 82, in the L direction.

The hooks 66, 100 of the rail 64 and of the rods 94, 96 are essentially identical, and, when the rods 94, 96 are in the rest position, the slots 67, 103 of the hooks 66, 100 are level in a transverse direction T perpendicular to the L direction and to the axes R. Thus, with the hooks 66, 100 in this position, the finger 40 (FIG. 1) can be inserted into the slots 67, 103 and moved in the direction T to couple the finger 40 selectively with one of the hooks 66, 100, or disengage the finger 40 from the hooks 66, 100 and thus release the finger 40.

Operation of the support 6 is described below with reference to FIGS. 4-6, where the plates 46, 48 are shown in chain line for reasons of clarity.

In a first position (FIG. 4), the plates 46, 48 are in a first position in which their directions P are perpendicular to the direction L, and the levers 82, 83 extend obliquely at about 45° to the direction L.

Figure 5:
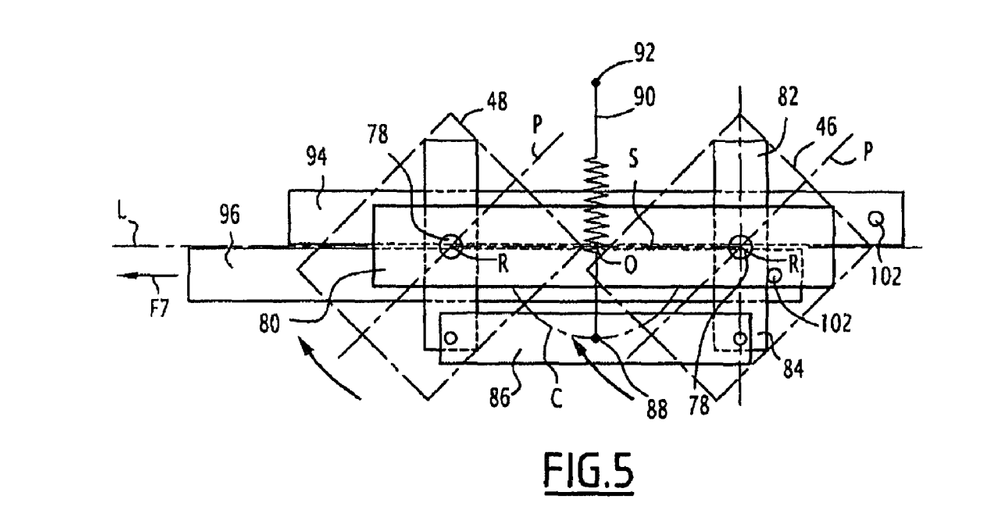

As shown in FIG. 5, the movement of rod 96 indicated by the arrow F7 brings the associated roller 102 into contact with the corresponding arm 84 of the drive lever 82, and the roller 102 turns the lever 82, thereby rotating the plate about the corresponding axis R.

Since the levers 82, 83 are connected by the link 86, the driven lever 83 and the corresponding plate 48 pivot simultaneously about the corresponding axis R.

The rod 96 continues to move until it reaches a second position (FIG. 6) in which the levers 82, 83 and the plates 46, 48 have pivoted through an angle of 90° from the first position. In this second position, the directions P of the plates are parallel to the direction L.

Figure 6:
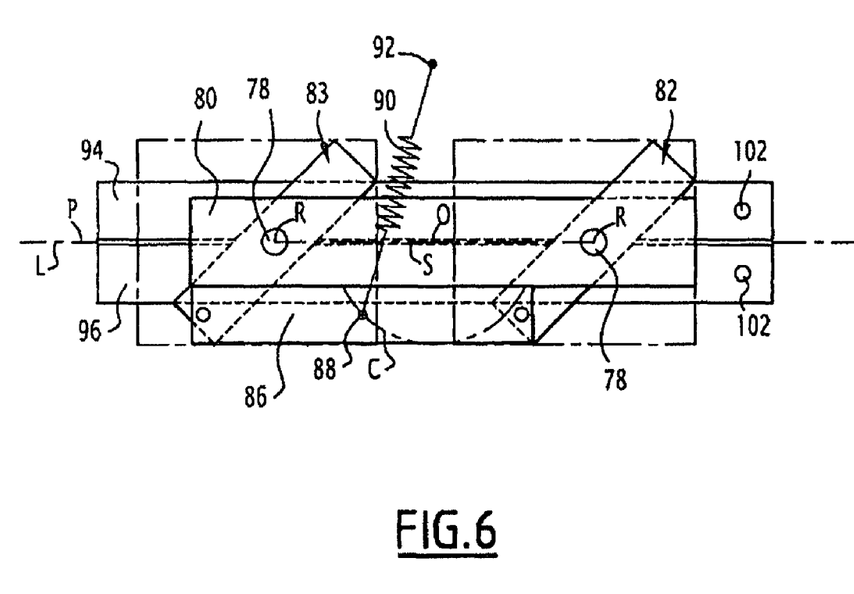

The rod 96 is returned to the rest position (FIG. 6).

Repeating the action on the same rod 96 produces no movement of the plates 46, 48.

Figure 4:
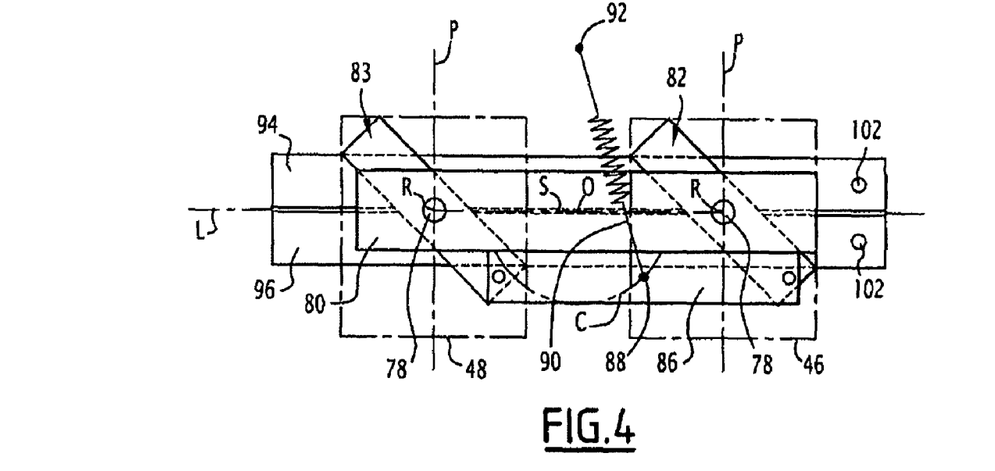
FIGS. 4-6 are schematic top views of the support shown in FIGS. 2 and 3, illustrating the operation of the control system.

Moving the other rod 94 produces an analogous rotation of the plates 46, 48 in the reverse direction, from the second position (FIG. 6) to the first (FIG. 4).

During the movements between the first and second positions, the pin 88 travels along an arc of a specific circle C whose center is a geometric point O situated on the line S. The attachment 92 is so positioned that, when the plates 46, 48 move from one position to the other, the distance between the pin 88 and the attachment 92 first increases and then decreases, passing en route through a maximum (FIG. 5) corresponding to a median intermediate position between the first and second positions of the plates 46, 48.

Therefore, when the plates 46, 48 are between the first position (FIG. 4) and the median position (FIG. 5), the spring 90 pulls the plates 46, 48 toward the first position (FIG. 4), and when the plates 46, 48 are between the second position (FIG. 6) and the median position (FIG. 5), the spring 90 pulls the plates 46, 48 toward the second position (FIG. 6). As a result, the plates 46, 48 are drawn to either the first or second position and do not stop between these positions.

In each of the first and second positions the link 86 is resting against a longitudinal face of the bar 80 and prevents the levers 82, 83, and therefore the plates 46, 48, from pivoting past the first and second positions.

The operation of the analyzing device 2 will now be described with reference to FIGS. 7-10.

Figure 7:
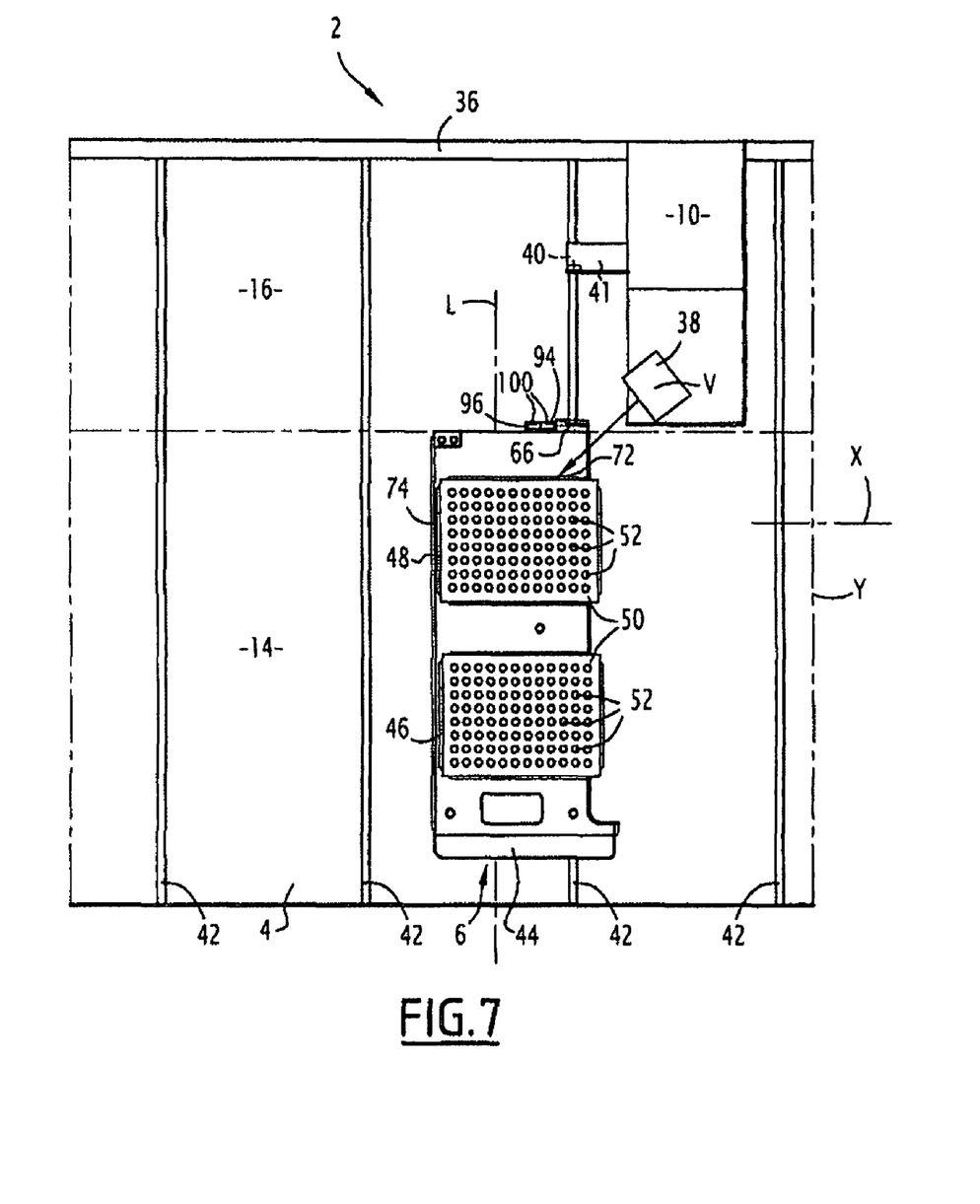
FIGS. 7-10 are schematic top views of the device shown in FIG. 1, illustrating its operation.

As illustrated in FIG. 7, the support 6 is positioned on the table 4 by engaging its rail 64 (not visible) on a track 42 mounted on the table 4. The L direction is therefore aligned with the Y direction, and the T direction (FIGS. 2 and 3) is aligned with the X direction.

The plates 46, 48 are in the first position.

The wells 52 of the plates 50 are filled with samples for analysis, e.g. blood.

The control unit 12 (FIG. 1) executes the analysis method by running the analysis program, using data previously entered via the control unit.

These data include, for example, without limitation, the position of the reagent vessels 18 (FIG. 1), the identification code of the support 6, the identification codes of the trays 50, and the mixtures to be prepared in each well 52 of each tray 50.

The first step is to ensure that the plates 46, 48 are in the correct positions.

To do this, the actuator 10 moves in the X direction along the rail 36 toward the support 6. The actuator 10 moves its finger in the X direction to line it up in the X direction with the hooks 66, 100, and then moves in the X direction to engage the finger in the hook 100 of the rod 96. The actuator 10 then moves its finger 40 in Y direction to actuate the rod 96, thereby rotating the plates 46, 48 into the second position (FIG. 8), and releases the rod 96 into its rest position. Next, the actuator 10 moves in the X direction until its finger 40 is engaged in the hook of the rod 94, upon which it actuates and releases the rod with the finger 40, thereby causing the plates to return to the first position (FIG. 7). By this means, even if the plates 46, 48 were not correctly positioned at the start, they are now in the first position.

The second step is for the actuator 10 to orient the reader 38 toward the tab 72 in order to detect its presence or absence. If the tab 72 is detected, this means that the plates 46, 48 are oriented correctly. If not, the actuator 10 returns to the first step. A second failure would mean there was some anomaly and would cause the process to halt. The detector reads from a considerable distance, and at a large angle of incidence, which is detrimental to an accurate reading. Nevertheless, the reading is sufficiently accurate to detect the orientation of the plates 46, 48.

Figure 9:
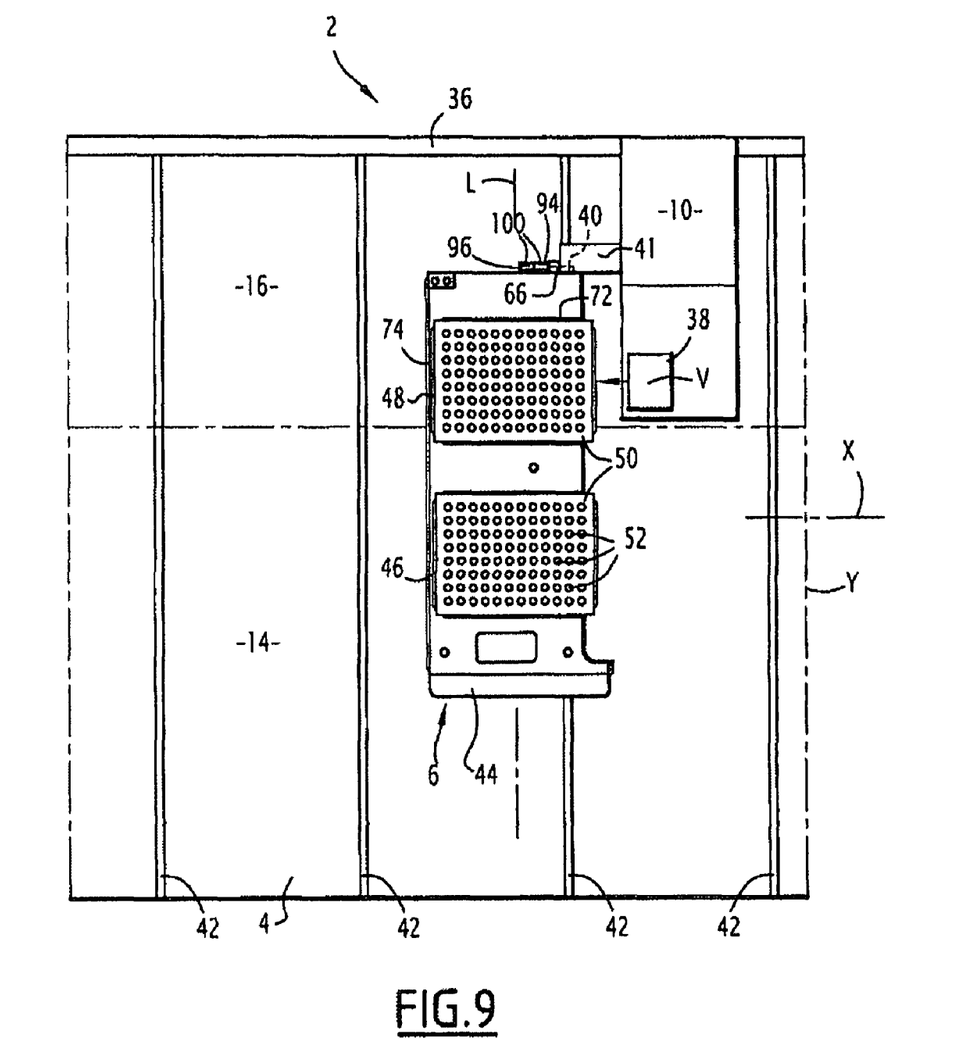

The third step is for the actuator to pull the support 6 into area 16 by hooking its finger 40 onto the hook 66 and bringing the identification codes of the trays 50 in front of the reader so that the codes can be read and the trays 50 identified (FIG. 9).

The reading is taken from the desired distance and at the desired angle of incidence. The reading is therefore accurate and reliable, ensuring correct identification of the trays 50. It is important because the samples must not become mixed up. If there is no code or if there are other anomalies, the process is interrupted.

The support 6 is returned to area 14 by the actuator 10.

In the fourth step the dispensing unit 8 (FIG. 1) takes reagents from the reagent vessels 18 (FIG. 1) by means of the pipettes 30 (FIG. 1), and fills the wells 52 of the tray 50 with these reagents.

Since the pipettes are lined up in a row in the Y direction, four wells 52 in one column on each tray 50 are filled simultaneously.

These operations are carried out until all the wells 52 have been filled.

Figure 8:
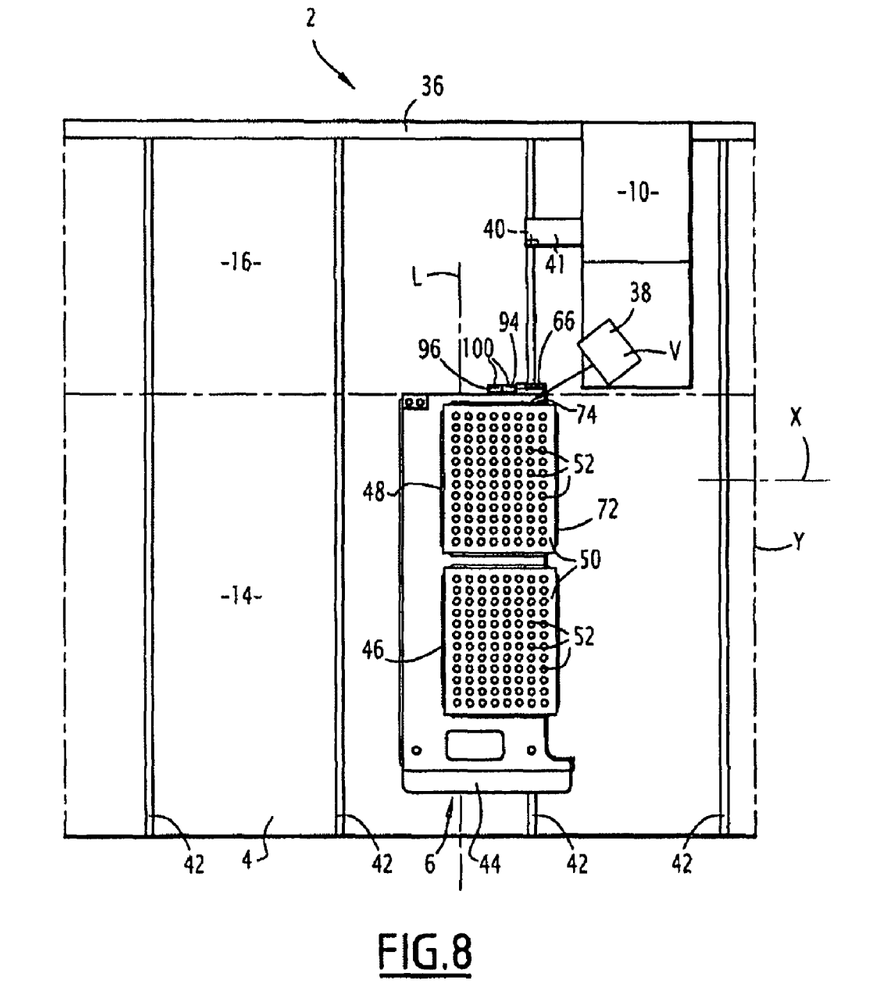

In the fifth step the actuator 10 uses its finger 40 to activate the rod 96 to pivot the plates 46, 48 into their second position (FIG. 8).

In the sixth step, which is similar to the second step, the actuator 10 orients its reader 38 and checks that the plates 46, 48 are at the correct angle by reading the tab 74 (FIG. 8).

Figure 10:
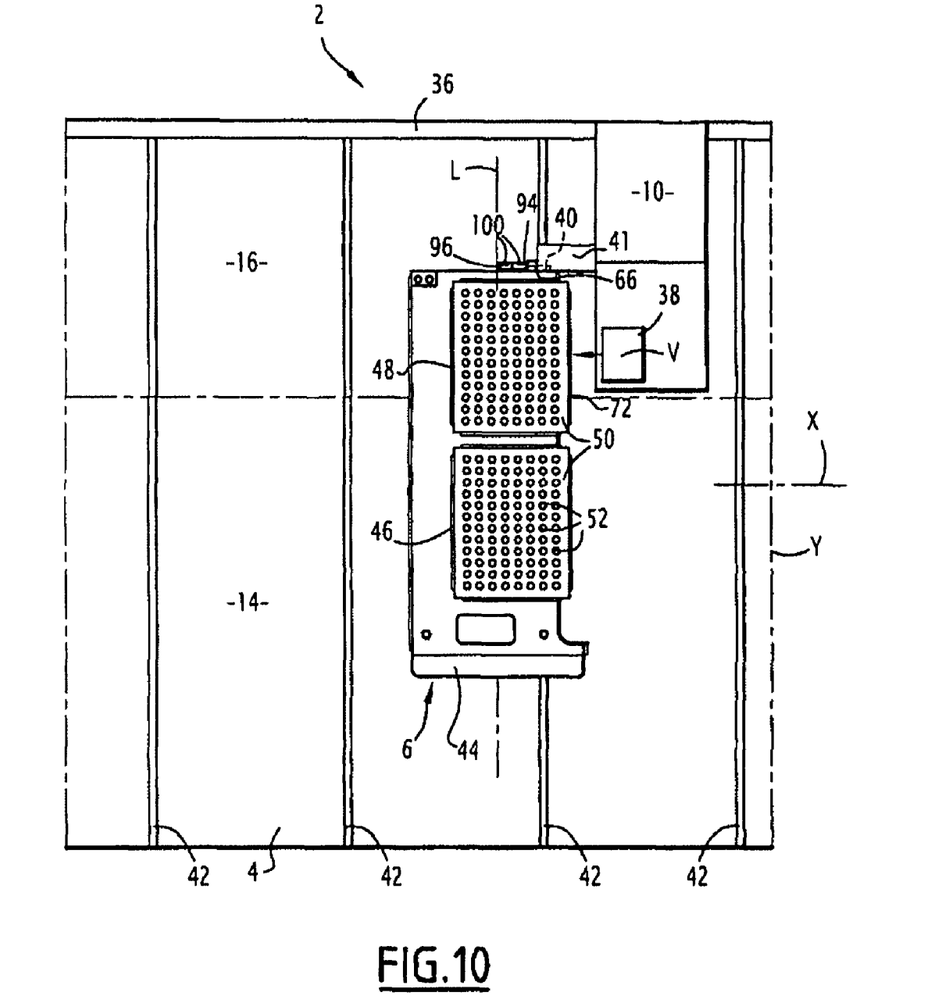

In the seventh step, which is similar to the third step, the actuator 10 pulls the support 6 into area 16 using its finger 40 hooked onto the hook 66 of the rail 64, so as to position the identification codes of the trays 50 in front of the reader 38 for the codes to be read and the trays 50 to be identified (FIG. 10).

The reference edges 68, 70 of a plate 46, 48 are equidistant from the axis of rotation R of the plate 46, 48, so the reference edges 68, 70 lie in the same reading plane in the first and second positions of the plate, respectively. The required reading conditions are therefore met, as in the third step.

If the third step was validated, but the seventh is not validated, as for example if the code is absent, this may mean that a tray 50 is incorrectly oriented on a plate 46, 48. If so, the analysis must be interrupted.

In a variant, steps similar to steps five to seven can be carried out before the fourth step, to detect incorrect orientation of the tray on its plate as soon as possible and avoid filling the wells 52 incorrectly.

The seventh step is an optional additional verification step. In a variant, the seventh step is not performed.

In the eighth step the dispensing unit takes reagents from the reagent vessels 18 (FIG. 1) using the pipettes (FIG. 1) and fills the wells 52 with these reagents.

With the orientation of the trays 50 in the second position of the plates, four wells 52 in a line on each tray 50 are filled simultaneously.

These operations are carried out until all wells 52 have been filled.

As a result, the reading actuator 10 of the analysis apparatus 2 is advantageously used to actuate the rods 94, 96 of the support 6 and so pivot the plates 46, 48.

Pivoting the plates allows rapid matrix-like filling of the wells 52.

The support 6 is simple and reliable, and enables an analysis method to be carried out reliably and repeatably.

This method is an example of a possible method. In a variant, the wells 52 are first filled row by row and then column by column.

In a variant, the dispensing head 20 has an actuating finger able to engage with the hooks 100, so that the rods 94, 96 can be actuated by the dispensing head 20.

The invention applies to the supporting of microassay trays, and in general to the supporting of reaction vessels comprising wells or test tubes laid out in a horizontal plane, e.g. in a matrix.

The invention claimed is:

1. A reaction vessel support of the type comprising a chassis (44) designed to be mounted in an analyzing device (2) and at least one supporting plate (46, 48) designed to take one or more reaction vessels (50), the supporting plate (46, 48) being mounted rotatably on the chassis (44) about an axis of rotation (R), the support being characterized in that it comprises at least one control member (94, 96) mounted movably on the chassis and comprising releasable means (100) of coupling to a movable actuating element (40) of an actuator (10) of the analyzing device (2) that can be moved to cause the movable actuating element to engage with the control member or disengage it from the control member, in such a way as to enable the control member (94, 96) to be moved by the actuator (10), with the control member (94, 96) and the supporting plate (46, 48) being connected together by mechanical drive elements (102, 82, 83), in such a way that a movement of the control member (94, 96) by the actuator (10) is able to bring about a rotation of the supporting plate (46, 84) about the axis of rotation (R) in at least one direction of rotation.

2. The support according to claim 1, characterized in that the mechanical drive elements (102, 82, 83) are housed inside the chassis (44).

3. The support according to one of claim 1, characterized in that the supporting plate (44, 48) is movable between two extreme positions forming an angle of 90° to each other.

4. The support according to claim 3, characterized in that it comprises return elements (86, 88, 90, 92) designed to return the supporting plate (46, 48) to a first extreme position when the supporting plate (46, 48) is between the first extreme position and a particular intermediate position between the two extreme positions, and to return the supporting plate (46, 48) to the second extreme position when the supporting plate is between the second extreme position and the intermediate position.

5. The support according to claim 4, characterized in that the return elements comprise a component (86) linked in movement to the supporting plate (46, 48), and an elastic return member (90) extending between the component (86) and a fixed attachment (92) on the chassis (44), the component (80) possessing a trajectory which passes through a position of greatest distance from the attachment (92) when the supporting plate (46, 48) is in the intermediate position.

6. The support according to claim 1, characterized in that the control member or each control member (94, 96) is mounted on and slides in the chassis (44).

7. The support according to claim 6, characterized and in that the drive elements comprise a roller (102) and a lever, one being connected to the control member or to each control member (94, 96), and the other being connected to the supporting plate (46, 48).

8. The support according to claim 1, characterized in that it comprises a control member (94) for moving the supporting plate (46, 48) in one direction of rotation, and another control member (96) for moving the supporting plate (46, 48) in the opposite direction of rotation, the releasable means (100) of coupling the control members (94, 96) being designed to be selectively engaged by the movable actuating element (40) of an actuator (10) belonging to the analyzing device.

9. The support according to claim 1, characterized in that the supporting plate (46, 48) comprises means of identification (72, 74) enabling the orientation of the supporting plate (46, 48) about its axis of rotation (R) to be identified.

10. An analyzing device (2) comprising a table (4) and a dispensing unit (8), the latter comprising a dispensing head (20) that is movable relative to the table (4) and possesses a row of pipettes (20) designed to draw up, retain and/or eject liquid, the device being characterized in that it comprises at least one reaction vessel tray support (6) according to claim 1, the chassis (44) being designed to be mounted on the table (4) in such a way as to allow a reaction vessel (50) carried by the support (6) to be filled, and at least one actuator (10) comprising a movable actuating element (40) designed to be engaged with the releasable coupling means (100) of the control member or each control member (94, 96) of the support (6).

11. The support according to claim 9, characterized in that the actuator (10) and the support (6) comprise releasable coupling means for moving the support (6) relative to the table (4).

12. The device according to claim 10, characterized in that the actuator (10) comprises means (38) for reading identification codes on a reaction vessel.

13. The device according to claim 12, characterized in that the supporting plate (46,48) comprises means of identification (72, 74) enabling the orientation of the supporting plate (46, 48) about its axis of rotation (R) to be identified and being of the same type as the identification codes of the reaction vessels designed to be placed on the support (6).

14. A method of using analyzing device (2), comprising a table (4) and a dispensing unit (8), the latter comprising a dispensing head (20) that is movable relative to the table (4) and possesses a row of pipettes (20), the analyzing device (2) being characterized in that it comprises at least one reaction vessel tray support (6) comprising a chassis (44) designed to be mounted in an analyzing device (2) and at least one supporting plate (46, 48) designed to take one or more reaction vessels (50), the supporting plate (46, 48) being mounted rotatably on the chassis (44) about an axis of rotation (R), the support being characterized in that it comprises at least one control member (94, 96) mounted movably on the chassis and comprising releasable means (100) of coupling to a movable actuating element (40) of an actuator (10) of the analyzing device (2) that can be moved to cause the movable actuating element to engage with the control member or disengage it from the control member, in such a way as to enable the control member (94, 96) to be moved by the actuator (10), with the control member (94, 96) and the supporting plate (46, 48) being connected together by mechanical drive elements (102, 82, 83), for analyzing samples distributed in wells in an analysis vessel carried by the support (6), comprising the following steps:

controlling the actuator to act on the control member or a control member (94, 96) of the pg,26 support (6) in order to place the supporting plate (46, 48) in a first position;

using the dispensing unit (8) to fill the wells;

controlling the actuator (10) to act on the control member or a control member (94, 96) of the support in order to place the supporting plate (46, 48) in a second position by pivoting it through an angle of approximately 90° about the axis of rotation (R) of the support (6); and using the dispensing unit (8) to fill the wells.

15. A computer program product for using an analyzing device, the computer program product comprising a non-transitory computer usable storage medium having computer readable program code embodied in the medium, the computer readable program code comprising software steps for executing the method of claim 14.

* * * * *